US006424856B1

United States Patent
Vilsmeier et al.

(10) Patent No.: US 6,424,856 B1
(45) Date of Patent: Jul. 23, 2002

(54) METHOD FOR THE LOCALIZATION OF TARGETED TREATMENT AREAS IN SOFT BODY PARTS

(75) Inventors: Stefan Vilsmeier, Poing; Rainer Birkenbach, Feldkirchen, both of (DE)

(73) Assignee: BrainLAB AG, Heimstetten (DE)

( * ) Notice: Subject to any disclaimer, the term of this patent is extended or adjusted under 35 U.S.C. 154(b) by 0 days.

(21) Appl. No.: 09/313,148

(22) Filed: May 17, 1999

(30) Foreign Application Priority Data

Jun. 30, 1998 (DE) .......................... 198 29 224

(51) Int. Cl.$^7$ ................................ A61B 5/05
(52) U.S. Cl. ................ 600/426; 600/429; 600/431; 128/899; 382/128; 250/363.2; 364/413.13; 324/309; 324/318
(58) Field of Search .................. 606/130; 600/426, 600/407, 410, 414, 417, 420, 429, 431; 128/899; 382/128; 250/363.2; 364/413.13; 324/309, 318

(56) References Cited

U.S. PATENT DOCUMENTS

| 5,389,101 A | * | 2/1995 | Heilbrun et al. ............ 606/130 |
| 5,961,457 A | * | 10/1999 | Raylman et al. ............ 600/436 |
| 5,967,980 A | * | 10/1999 | Ferre et al. .................. 600/424 |
| 6,006,126 A | * | 12/1999 | Cosman ....................... 600/426 |
| 6,246,898 B1 | * | 6/2001 | Vesely et al. ................ 600/424 |

* cited by examiner

Primary Examiner—Marvin M. Lateef
Assistant Examiner—Jeoyuh Lin
(74) Attorney, Agent, or Firm—Renner, Otto, Boisselle & Sklar, LL

(57) ABSTRACT

A method for localization of surgical target sites in the region of soft body parts, including the following steps: applying a number of artificial landmarks to the body part permitting sensing by a referencing system; referencing the surgical target site location relative to a landmark arrangement in a first position of the body part; sensing a new landmark arrangement in a changed second position of the soft body part; and mapping the dislocation or new location of the surgical target site by means of the information as to the dislocation or new arrangement of the landmarks.

13 Claims, 1 Drawing Sheet

METHOD FOR THE LOCALIZATION OF TARGETED TREATMENT AREAS IN SOFT BODY PARTS

BACKGROUND OF THE INVENTION

1. Field of the Invention

The invention relates to a method for the localization of targeted treatment areas, i.e. surgical target sites in soft body parts.

In lesion analysis and surgery, knowing the precise location of the lesion is naturally of vital importance. Where relatively rigidly structured parts of the body are concerned it has been possible for quite some time to map the position of a lesion relatively accurately in any position of the body via referencing with artificial or natural landmarks so that the surgeon is able to operate or apply radiation therapy with the aid of computer-assisted mapping systems. This is possible more particularly because the location of a lesion in relatively rigid tissue hardly changes its position relative to artificial landmarks applied, for example, to the skin in the surroundings, even when there is a more pronounced change in the position of the body.

This, is, however, much more of a problem when needing to precisely localize surgical target sites in the region of soft parts of the body, such as e.g. in the female breast, whereby breast cancer is the most frequent type of cancer illness.

2. Description of Prior Art

Conventionally, tactile sensing of a lesion in a soft part of the body is repeatedly needed to establish its location and roughly its shape, and to be able to carry out, for example, with relatively accuracy a biopsy or radiation treatment. There is, of course, also the possibility of securing the body part to the remainder of the body, for example, by means of strips of plaster which is, however, usually troublesome to the patient.

A further disadvantage of the conventional method in tactile lesion localization is that due to the inherent inaccuracy in biopsies it is often impossible to remove tissue at the correct location right from the start, thus necessitating several operations and the attendant pain thereof.

SUMMARY OF THE INVENTION

It is the object of the present invention to provide a method for the localization of surgical target sites in soft body parts which obviates the disadvantages of conventional methods as cited above. More particularly it is the intention to provide a localization method which permits precise mapping of the site also during surgery despite changes in position.

This object is achieved in accordance with the invention by a method for the localization of surgical target sites in soft body parts comprising the following steps:

Applying a number of artificial landmarks to the body part permitting sensing by a referencing system;

Referencing the surgical target site location relative to a landmark arrangement in a first position of the body part;

Sensing a new landmark arrangement in a changed second position of the soft body part; and Mapping the dislocation or new location of the surgical target site by means of the information as to the dislocation or new arrangement of the landmarks.

In other words, the new location and, to advantage, also the new shape of the surgical target site is thus determined from the landmark position before and after the change in shape of the soft body part. It is of advantage that in accordance with the invention there is now no need for tactile resensing the location of the lesion, and no painful means of securing its location need to be made. The discomfort involved therein for the patient is thus avoidable by means of the invention. No additional dislocation is caused by sensing so that biopsies or radiation treatment may now be implemented with enhanced accuracy.

In one preferred embodiment of the method in accordance with the invention the landmark arrangement comprises at least three landmarks to enable their relatively position to be established three-dimensionally with sufficient accuracy.

In another preferred embodiment of the method in accordance with the invention for referencing in the first position a mapping system, more particularly a computer-assisted mapping system, preferably a CT, MRI, PET or SPECT mapping system is used by means of which the artificial landmarks as well as the structure of the body part may be mapped.

Thus, in preparation for subsequent surgery the location of the lesion relative to the arrangement of the landmarks is mapped for example by means of a computer tomograph to enable any change in position of the surgical target site to be later determined from the change in position of the landmarks. The resulting data may be stored for repeated use during surgery.

Preferably, to map the new landmark arrangement in the changed second position of the soft body part in accordance with the invention a computer-assisted mapping system is employed which monitors the surgery site.

Thus, when the patient after presurgery preparation is brought into the operating theater for actual surgery the new location of the landmarks relative to each other is established by a mapping system which, for example, maps the location of the artificial landmarks with a camera system and a computer processes the information for output on a monitor, the computer system thus "seeing" the arrangement of the landmarks in the first and in the second position and enabling this data to be analyzed.

For this purpose use is made in a particularly preferred embodiment of the invention of a system of coordinates as dictated by the landmark arrangement for sensing the dislocation or new location of the surgical target site, whereby by means of a transformation model working on the basis of modelled structure data for the body part the new coordinate location of the surgical target site is calculated computer-assisted.

Once the three-dimensional location of the individual landmarks relative to each other is known prior to and after the change in position of the soft body part, it can also be computed what has happened in the interior of the soft body part in it being changed in position, i.e. what location or change in shape the internal surgical target site has assumed. For this purpose use may be made for example of a mechanomathematical shaping model which simulates the soft body part for example as a jelly-like mass. From the knowledge of the outer deformation of such a mass (dislocation of the landmarks relative to each other) the inner change in position may then also be computed and thus the new location as well as the new shape of the lesion.

The method in accordance with the invention proves to be particularly of advantage when each actual location is newly computed continually on a real-time basis and continually displayed updated on a computer monitor. The surgeon, for example in a biopsy, is then able to keep track of all changes in position of the lesion with a tissue removal instrument likewise referenced in the operating theater and to obtain the tissue specimen from the desired location without necessitating multiple intervention.

The method in accordance with the invention is applicable to particular advantage in localizing lesions in the region of the female breast, especially in the case of breast cancer.

BRIEF DESCRIPTION OF THE DRAWINGS

The method will now be discussed in detail with reference to the drawings in which:

Referring now to FIG. 1 there is illustrated a soft body part identified by the reference numeral 1 including a lesion 2. Attached to the outer side of the body part 1, i.e. for example to the skin of the patient, are artificial landmarks 3, four of which are evident as shown in FIG. 1.

FIG. 1 represents, for example, the condition in which the soft body part is slice-scanned by means of a computer tomograph to map both the position of the landmarks 3 and the position of the lesion 2, the location of the one relative to the other being computed so that the position of the lesion 2 is known in the system of coordinates of the landmarks 3.

Referring now to FIG. 2 there is illustrated the soft body part is a changed location, i.e. for example after the computer tomograph of the patient who is now in the operating theater (for example for implementation of a biopsy). It is evident from FIG. 2 that due to the dislocation of the soft body part 1 the position and shape of the lesion 2 have also changed. However, there as also been a likewise change in the arrangement of the landmarks 3 and now in accordance with the invention, once the new location of the landmarks 3 relative to each other has been mapped in the operating position, the new location of the lesion 2 may be computed when a sufficiently accurate mechanomathematical deformation or transformation model is employed which simulates the body part 2 for example as a jelly-like mass.

Figure 1:
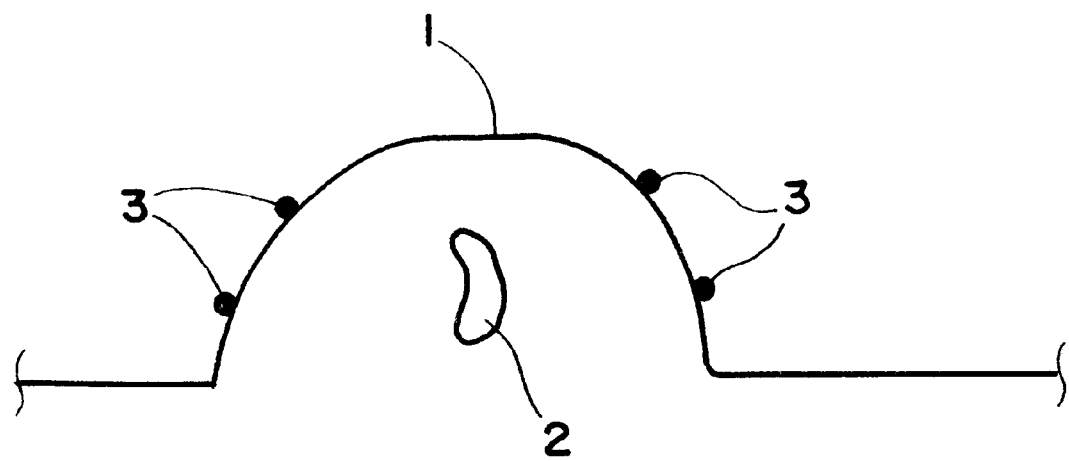
FIGS. 1 and 2 depict a soft body part having a lesion in a first position (FIG. 1) and in a second position (FIG. 2).
Figure 2:
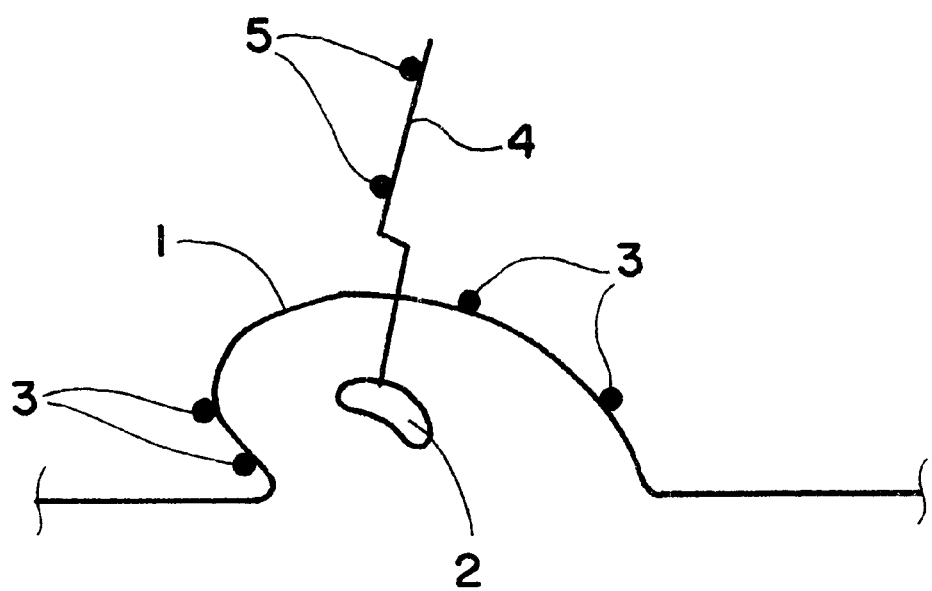

The new status of the location may be displayed via a computer and a monitor in real time as a visual operating aid for the surgeon who is now able to implement a targetted biopsy by means of a tissue removal instrument 4 including mappable markings 5 likewise referenced three-dimensionally as shown schematically in this case.

Even if there is a further dislocation of the lesion 2 during the biopsy the surgeon is still able to keep track thereof with no problem on the computer display in real time and there is no longer the risk of healthy tissue possibly being removed accidentally.

List of Reference Numerals 1. body part
2. surgical target site
3. landmark
4. tissue removal instrument
5. marking

What is claimed is:

1. A method for localization of a surgical target site in the region of a soft body part comprising the following steps:

applying a number of artificial landmarks to the soft body part thereby to permit sensing by a referencing system;

referencing the surgical target site location relative to a first arrangement of the landmarks in a first position of the soft body part;

sensing a second arrangement of the landmarks in a second position of the soft body part different from the first position of the soft body part; and mapping the dislocation or new location of the surgical target site by using modeled structure data for the soft body part which relates changes within the interior of the soft body part to changes in the arrangement of the landmarks.

2. The method as set forth in claim 1, wherein at least three landmarks are applied to the soft body part.

3. The method as set forth in claim 2, wherein the second arrangement of the landmarks in said second position of said soft body part is sensed by a computer-controlled mapping system which monitors the surgery site.

4. The method as set forth in claim 2, wherein a lesion in the region of the female breast is localized.

5. The method as set forth in claim 1, wherein the referencing step includes using a CT, MRI, PET or SPECT mapping system to map the artificial landmarks and the structure of said soft body part.

6. The method as set forth in claim 5, wherein the second arrangement of the landmarks in said second position of said soft body part is sensed by a computer-controlled mapping system which monitors the surgery site.

7. The method as set forth in claim 5, wherein a lesion in the region of the female breast is localized.

8. The method as set forth in claim 1, wherein the second arrangement of the landmarks in said second position of said soft body part is sensed by a computer-controlled mapping system which monitors the surgery site.

9. The method as set forth in claim 8, wherein a lesion in the region of the female breast is localized.

10. The method as set forth in claim 1, wherein a lesion in the region of the female breast is localized.

11. The method as set forth in claim 1, wherein the dislocation or new location of the surgical target site is mapped continuously on a real-time basis and displayed in real time on a computer monitor.

12. The method as set forth in claim 11, wherein a lesion in the region of the female breast is localized.

13. The method as set forth in claim 1, wherein a lesion in the region of the female breast is localized.

* * * * *